United States Patent
Mohamed et al.

(10) Patent No.: US 11,734,819 B2
(45) Date of Patent: Aug. 22, 2023

(54) DEEP LEARNING MODELING USING HEALTH SCREENING IMAGES

(71) Applicant: Merative US L.P., Ann Arbor, MI (US)

(72) Inventors: Aly Mohamed, Acton, MA (US); Maria Victoria Sainz de Cea, Somerville, MA (US); David Richmond, Newton, MA (US)

(*) Notice: Subject to any disclaimer, the term of this patent is extended or adjusted under 35 U.S.C. 154(b) by 320 days.

(21) Appl. No.: 16/934,538

(22) Filed: Jul. 21, 2020

(65) Prior Publication Data

US 2022/0028058 A1 Jan. 27, 2022

(51) Int. Cl.
*G06T 7/00* (2017.01)
*G16H 50/20* (2018.01)
*G16H 50/30* (2018.01)
*G06F 18/214* (2023.01)

(52) U.S. Cl.
CPC .......... *G06T 7/0012* (2013.01); *G06F 18/214* (2023.01); *G16H 50/20* (2018.01); *G16H 50/30* (2018.01); *G06T 2207/10116* (2013.01); *G06T 2207/20081* (2013.01); *G06T 2207/20084* (2013.01); *G06T 2207/30068* (2013.01)

(58) Field of Classification Search
CPC ......... G06T 7/0012; G06T 2207/10116; G06T 2207/20081; G06T 2207/20084; G06T 2207/30068; G06K 9/6256; G16H 50/20; G16H 50/30; G16H 30/40; G16H 40/67; G16H 50/70; G06V 10/25; G06V 10/774; G06V 2201/03; G06V 10/82
USPC ........................................................ 382/128
See application file for complete search history.

(56) References Cited

U.S. PATENT DOCUMENTS

| | | | | |
|---|---|---|---|---|
| 2005/0049497 A1* | 3/2005 | Krishnan | ............... | G16H 50/20 600/437 |
| 2008/0159613 A1* | 7/2008 | Luo | .......................... | G06T 7/12 382/132 |
| 2009/0296999 A1* | 12/2009 | Raundahl | ............. | G06V 10/763 382/128 |
| 2016/0364526 A1* | 12/2016 | Reicher | ................. | G06F 18/213 |
| 2017/0091937 A1* | 3/2017 | Barnes | ................. | G06V 10/771 |
| 2017/0249739 A1* | 8/2017 | Kallenberg | ....... | G06F 18/24143 |
| 2018/0214086 A1* | 8/2018 | Park | ..................... | A61B 6/5217 |
| 2019/0027252 A1* | 1/2019 | Calhoun | ............... | G06T 7/0012 |
| 2019/0220978 A1* | 7/2019 | Moehrle | ............... | G06T 7/0014 |

(Continued)

FOREIGN PATENT DOCUMENTS

WO 2008157843 A1 12/2008

OTHER PUBLICATIONS

Perek, S., et al., "Learning from Longitudinal Mammography Studies." Published Online Oct. 10, 2019. 9 pages. Published by MICCAI. https://link.springer.com/chapter/10.1007%2F978-3-030-32226-7_79.

(Continued)

*Primary Examiner* — Van D Huynh
(74) *Attorney, Agent, or Firm* — Stephen J. Walder, Jr.

(57) ABSTRACT

An AI system may receive an image. The AI system may include a first AI model trained using labeled training images including images from prior mammograms to predict cancer and a second AI model trained using labeled training images including images from current mammograms to classify mammogram images. The second AI model may be initialized using the weights of the first AI model using transfer learning. The AI system may receive a classification output indicating a likely current breast cancer diagnosis or a likelihood of the user to develop breast cancer in the future.

25 Claims, 6 Drawing Sheets

(56) References Cited

U.S. PATENT DOCUMENTS

2020/0178918 A1\* 6/2020 Park .................. A61B 6/563
2021/0093301 A1\* 4/2021 Wang ................ G06V 10/764

OTHER PUBLICATIONS

Arefan, D., et al., "Deep learning modeling using normal mammograms for predicting breast cancer risk." Published Nov. 19, 2019. 9 pages.
Park, J., et al., "Screening Mammogram Classification with Prior Exams." Published Jul. 30, 2019. 5 pages. Published by ARXIV. https://arxiv.org/abs/1907.13057.
Santeramo, R., et al., "Longitudinal detection of radiological abnormalities with time-modulated LSTM." Published Jul. 16, 2018. 10 pages. Published by ARXIV. https://arxiv.org/abs/1807.06144.
Wang, J., et al., "Discrimination of Breast Cancer with Microcalcifications on Mammography by Deep Learning." Published Jun. 7, 2016. 9 pages. Published by Scientific Reports.
Wu, N., et al., "Deep Neural Networks Improve Radiologists' Performance in Breast Cancer Screening " Published Mar. 8, 2019. 19 pages. Published by ARXIV. https://arxiv.org/abs/1903.08297.
Yala, A. et al., "A Deep Learning Mammography-based Model for Improved Breast Cancer Risk Prediction." Published Online May 7, 2019. 7 pages. Radiology, vol. 292. Published by RSNA. https://pubs.rsna.org/doi/10.1148/radiol.2019182716.
Mell et al., "The NIST Definition of Cloud Computing," Recommendations of the National Institute of Standards and Technology, U.S. Department of Commerce, Special Publication 800-145, Sep. 2011, 7 pgs.

\* cited by examiner

DEEP LEARNING MODELING USING HEALTH SCREENING IMAGES

BACKGROUND

The present disclosure relates generally to the field of medical imaging, and more specifically to deep learning modeling using current and prior medical images from health screenings.

Medical imaging is used during health screenings to screen for medical conditions. A patient may receive periodic health screenings, for example, yearly, for early detection, particularly for medical conditions where early detection plays an important role in treatment. Digital mammography is a standard screening exam of breast cancer in the general population. A mammogram can detect breast cancer before the tumor can be felt by a patient or detected by a doctor. Breast cancer detection in screening mammography is affected by the experience level of the radiologist, the sub-specialization of the radiologist, and the volume of images that the radiologist reviews in a given time. Artificial intelligence (AI) deep learning approaches can help radiologists in their decision-making and reduce subjective intra-reader and inter-reader variation.

Training deep learning models to detect something in a medical image that indicates that a patient may have cancer, for example, a tumor, is challenging as tumors are small and look similar to other anomalies in a medical image. A few pixels of an image could, or could not, indicate that a patient is likely to have cancer. Training deep learning models to detect something in a medical image that indicates that a patient may develop cancer in the future is even more challenging. To be helpful in early detection and diagnosis, deep learning models need to be trained to detect anomalies indicating a likely cancer diagnosis or a likely future cancer diagnosis with the limited set of training data available.

SUMMARY

Embodiments of the present disclosure include a method, computer program product, and system for deep learning modeling using current and prior medical images from health screenings.

In some embodiments, an AI system may receive a user image. The AI system may include a first AI model trained using labeled training images from prior health screenings to predict a medical condition and a second AI model trained using labeled training images from current health screenings to classify images. The AI system may receive a classification output.

In some embodiments, the second AI model is trained by, after the first AI model is trained to predict the medical condition, using transfer learning to apply the weights from the first AI model to initialize the second AI model.

In some embodiments, the images from the current health screenings are images from one or more first users who received positive diagnoses within a first time period from the current health screenings being taken.

In some embodiments, the images from the prior health screenings are images from one or more second users who received negative screenings for at least a second time period following the prior health screenings being taken and later received positive diagnoses.

In some embodiments, the user image is a digital x-ray.

In some embodiments, the first AI model is a convolutional neural network.

In some embodiments, the second AI model is a convolutional neural network.

In some embodiments, an AI system may receive an image. The AI system may include a first AI model trained using labeled training images including images from prior mammograms to predict cancer and a second AI model trained using labeled training images including images from current mammograms to classify mammogram images. The second AI model may be initialized using the weights of the first AI model using transfer learning. The AI system may receive a classification output indicating a likely current breast cancer diagnosis or a likelihood of the user to develop breast cancer in the future.

In some embodiments, the user image is a digital mammogram.

In some embodiments, the current mammograms are one or more medical images from one or more first users who received positive cancer diagnoses within a first time period from the medical images being taken.

In some embodiments, the prior mammograms are one or more further medical images from one or more second users who received negative cancer screenings for at least a second time period following the medical image being taken and later received positive diagnoses.

In some embodiments, the first AI model and the second AI model are convolutional neural networks.

In some embodiments, a processor of an AI system may receive training images. Each of the images may be linked in a group, where the group includes training images of one training user. The processor may register the grouped training images. Registering grouped training images may involve aligning a first training image so that the same region of 2D space in the first training image in the group can be compared to a same region of 2D space in a second training image in the group. The processor may obtain a first set of feature vectors from a first AI model trained to predict cancer using training images from prior mammograms. The processor may obtain a second set of feature vectors from a second AI model trained to classify images using training images from current mammograms. The processor may apply a feature selection algorithm to the first set of feature vectors and the second set of feature vectors. The processor may input feature vectors selected using the feature selection algorithm into a classification AI model. The processor of the AI system may provide an output, where the output includes a first prediction score indicating a likelihood of future breast cancer development and a second classification score indicating likelihood of current cancer.

In some embodiments, the current mammograms are one or more medical images from one or more first users who received positive diagnoses within a first time period from the medical images being taken.

In some embodiments, the prior mammograms are one or more further medical images from one or more second users who received negative screenings for a second time period following the medical images being taken and later received positive diagnoses.

In some embodiments, the second AI model is trained by, after the first AI model is trained to predict breast cancer, using transfer learning to apply the weights from the first AI model to initialize the second AI model.

In some embodiments, the first AI model and the second AI model are convolutional neural networks.

In some embodiments, the classification AI model is a Long Short-Term Memory.

In some embodiments, a system comprising a memory and processor is provided. In some embodiments, the processor is in communication with the memory. In some embodiments, the processor is configured to receive training images, where each of the training images is linked in a group, and where the group includes training images of one training user. In some embodiments, the processor is configured to obtain a first set of feature vectors from a first AI model trained to predict cancer using training images from prior mammograms. In some embodiments, the processor is configured to obtain a second set of feature vectors from a second AI model trained to classify images using training images from current mammograms. In some embodiments, the processor is configured to apply a feature selection algorithm to the first set of feature vectors and the second set of feature vectors. In some embodiments, the processor is configured to input feature vectors selected using the feature selection algorithm into a classification AI model. In some embodiments, the processor is configured to provide an output, where the output includes a first prediction score indicating a likelihood of future breast cancer development and a second classification score indicating likelihood of current cancer.

In some embodiments, the second AI model is trained by, after the first AI model is trained to classify images, using transfer learning to apply the weights from the first AI model to initialize the second AI model.

In some embodiments, the current mammograms are one or more medical images from one or more first users who received positive cancer diagnoses within a first time period from the medical images being taken.

In some embodiments, the prior mammograms are one or more further medical images from one or more second users who received negative cancer screenings for at least a second time period following the medical image being taken and later received positive diagnoses.

In some embodiments, a computer program product comprising a computer readable storage medium having program instructions embodied therewith, the program instructions executable by a processor to cause the processor to perform operations, is provided. In some embodiments, the processor is configured to receive training images, where each of the training images is linked in a group, and where the group includes training images of one training user. In some embodiments, the processor is configured to obtain a first set of feature vectors from a first AI model trained to predict cancer using training images from prior mammograms. In some embodiments, the processor is configured to obtain a second set of feature vectors from a second AI model trained to classify images using training images from current mammograms. In some embodiments, the processor is configured to apply a feature selection algorithm to the first set of feature vectors and the second set of feature vectors. In some embodiments, the processor is configured to input feature vectors selected using the feature selection algorithm into a classification AI model. In some embodiments, the processor is configured to provide an output, where the output includes a first prediction score indicating a likelihood of future breast cancer development and a second classification score indicating likelihood of current cancer.

In some embodiments, the current mammograms are one or more medical images from one or more first users who received positive cancer diagnoses within a first time period from the medical images being taken.

In some embodiments, the prior mammograms are one or more further medical images from one or more second users who received negative cancer screenings for at least a second time period following the medical image being taken and later received positive diagnoses.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
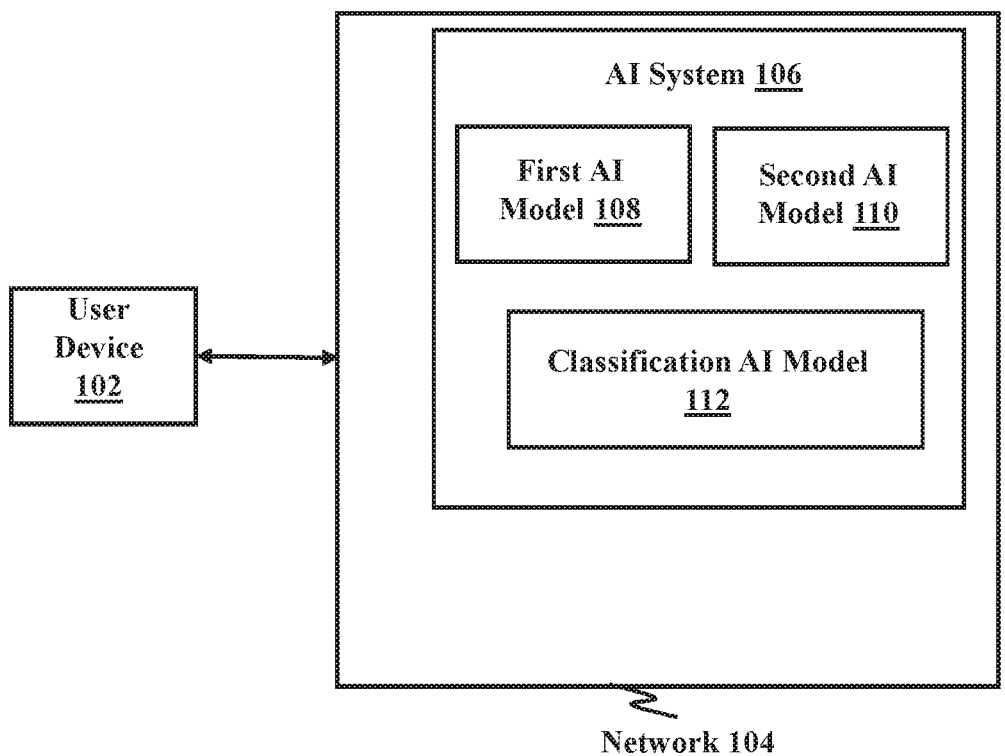
FIG. 1 is a block diagram of an exemplary system for improved health screening using artificial intelligence, in accordance with aspects of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

Aspects of the present disclosure relate generally to the field of medical imaging, and more specifically to deep learning modeling using current and prior medical images from health screenings. While the present disclosure is not necessarily limited to such applications, various aspects of the disclosure may be appreciated through a discussion of various examples using this context.

Medical imaging is used during health screenings to screen for medical conditions. A patient may receive periodic health screenings, for example, yearly, for early detection, particularly for medical conditions where early detection plays an important role in treatment. When a health screening (in which a medical image is taken) results in the diagnosis of a medical condition (either because of the results of the medical image or the results of subsequent tests, such as a biopsy), the medical image from that health screening (e.g., current health screening) can provide information useful for diagnosis of the medical condition. If a patient also had prior health screenings involving medical imaging, those medical images (e.g., prior health screenings) may also provide information useful for diagnosis of the medical condition.

The present disclosure is directed to deep learning modeling using current and prior medical images from health screenings, including medical images from mammograms, prostate cancer screenings, lung cancer screening, or any other health screenings for which patients receive multiple medical images over time. The present disclosure is directed to artificial intelligence deep learning approaches where a model is trained utilizing the health screenings (e.g., medical images and associated medical information) from which a patient received a medical diagnosis (e.g., current health screenings) as well as earlier health screenings before the medical diagnosis of the health condition was detected (e.g., prior health screenings). The artificial intelligent approaches of the present disclosure, therefore, involve two tasks: predicting a likelihood of an individual to develop a medical condition in the future and classifying an individual as likely to currently have the medical condition.

In some embodiments, an artificial intelligence ("AI") system (or a processor in the AI system) may receive a user image. For example, the user may have a health screening during which an image is generated that is used for clinical analysis and/or medical intervention. The image may be a medical image which reveals internal structures of the body hidden by the skin. The image may be a radiological image generated through imaging technologies, such as X-ray radiography, magnetic resonance imaging, ultrasound, endoscopy, elastography, tactile imaging, thermography, medical photography, and nuclear medicine functional imaging techniques as positron emission tomography (PET) and single-photon emission computed tomography (SPECT). In some embodiments, the user image may be a digital X-ray. In some embodiments, the user image may be a mammogram.

In some embodiments, the AI system may include a first AI model trained using labeled training images from prior health screenings to classify images as indicating a likelihood of the user to develop a medical condition in the future (positive) or not indicating a likelihood of the user to develop the medical condition in the future (negative). In some embodiments, the AI system may include a second AI model trained using labeled training images from current health screenings to classify images as indicating a likely current medical diagnosis (positive) or not indicating a likely current medical diagnosis (negative). In some embodiments, the first AI model and the second AI model are deep learning models used for image classification. In some embodiments, the first AI model is a convolutional neural network ("CNN"). In some embodiments, the second AI model is a CNN.

In some embodiments, the current health screenings may be a set of images obtained for training the second AI model which have been gathered retrospectively after the individuals from whom the images were taken have been diagnosed with the medical condition. In some embodiments, the second AI model is a model that has been trained to classify images as indicating a likely current diagnosis of a medical condition (e.g., it is likely that the user currently has the medical condition) or not indicating a likely diagnosis of the medical condition (e.g., it is likely that the user does not currently have the medical condition).

In some embodiments, the current health screenings are images from one or more first users who received positive medical diagnoses (e.g., from screenings, medical imaging, or other test results which indicate that they have the medical condition) within a first time period from the current health screenings being taken. As an example, the current health screenings may be medical images taken from one or more first users who were diagnosed with lung cancer after receiving a positive health screening and biopsy providing, or confirming, the lung cancer diagnosis within a 12 month time period after the medical images were taken. In some embodiments, the second AI model may also be trained using images which have been labeled as negative for the medical diagnosis (e.g., indicating that the user does not have cancer). The negative labeled images may be gathered from users for whom the screening exam (medical images and/or other testing) is negative (e.g., negative for cancer or benign) and follow-up screening exams (medical images and/or other testing) for a 24-48 months period are negative.

In some embodiments, the prior health screenings are a set of images obtained for training the first AI model to classify images as indicating a likelihood of the user to develop a medical condition (positive) or not indicating a likelihood of the user to develop a medical condition (negative). The images in the prior health screenings set of images may be images from one or more second users who received negative screenings (e.g., indicating that the users do not have the medical condition) for at least a second time period following the images from the prior health screenings being taken and later receive a positive diagnosis (e.g., indicating that the users do have the medical condition).

As an example, the prior health screenings may be medical images taken from one or more second users who were determined to not have lung cancer (e.g., either based on the medical images and/or other testing) for at least a 24-48 month time period after the time that the medical images in the set of prior health screenings were taken, and after that time period received a positive diagnosis (e.g., indicating that the users do have the medical condition, either by medical imaging, other diagnostic testing, or both).

In some embodiments, the one or more second users from whom the images in the prior health screenings set of images is obtained may partially, or completely, overlap with the one or more first users from whom the images in the current health screenings set of images is obtained. For example, user A may have 10 yearly health screenings during which medical images are obtained. If, in year 10, user A is diagnosed with cancer, the year 10 medical image may be included among the images of set of images from current health screenings. The year 1 through year 7 medical images may be included among the images of the set of images from the prior health screenings. In some embodiments, the first AI model may also be trained using images which have been labeled as not indicating a likelihood of the user to develop a medical condition (negative). The negative labeled images may be gathered from users who it was determined do not have the medical condition (e.g., by the medical images and/or other testing) for a time period greater than 48 months.

In some embodiments, the AI system may receive a classification output, where the classification output provides a classification by the first AI model, the second AI model, or both models. In some embodiments, the classification output may be an output of the AI system from the first AI model which provides information indicating a likelihood of the user to develop the medical condition in the future.

In some embodiments, the classification output may be an output from the second AI model which indicates a likely current medical diagnosis. For example, the classification output may be a numerical value which indicates that the user image is classified as: indicating a likelihood of the user to develop the medical condition in the future, indicating a likely current medical diagnosis, or indicating both a likelihood of the user to develop the medical condition in the future and indicating a likely current medical diagnosis.

Following the example, a medical image from a user may be provided to the AI system. The medical image may be a medical image of the lung. The lung may have a tumor and an abnormality which may develop into a tumor. The AI system may provide an output classifying the medical image as indicating a likelihood of the user to develop lung cancer in the future based on the first AI model classifying the abnormality on the lung as likely to develop into tumors. The AI system may provide an output classifying the medical image as indicating a likely current medical diagnosis based on the second AI model classifying the tumor as indicative of a positive cancer diagnosis.

In some embodiments, the second AI model is trained by, after the first AI model is trained to classify images, using transfer learning to apply the weights from the first AI model to initialize the second AI model. In other words, the second AI model is loaded using the pretrained weights from the first AI model. Use of transfer learning to initialize the second AI model with the weights of the first AI model may help train the second model more quickly, to be more accurate, and with the limited set of training data available to train the deep learning system.

In some embodiments, an AI system for improving breast cancer screening may receive a user image. For example, a user may have a health screening during which a mammogram may be generated that may be used for clinical analysis or medical intervention. In some embodiments, the user image may be a digital mammogram.

In some embodiments, the AI system may include a first AI model trained to classify images as indicating a likelihood of the user to develop breast cancer in the future (positive) or not indicating a likelihood of the user to develop breast cancer in the future (negative) using labeled training images including images from prior mammograms. In some embodiments, the AI system may include a second AI model trained to classify images as indicating a likely current diagnosis of breast cancer (positive) or not indicating a likely current diagnosis of breast cancer (negative) using labeled training images including images from current mammograms.

In some embodiments, the first AI model and the second AI model are deep learning models used for image classification. In some embodiments, the first AI model is a CNN. In some embodiments, the second AI model is a CNN. In some embodiments, the second AI model is trained by, after the first AI model is trained to classify images, using transfer learning to apply the weights from the first AI model to initialize the second AI model. In other words, the second AI model is loaded during training using the pretrained weights from the first AI model.

In some embodiments, the current mammograms are a set of images obtained for training the second AI model which have been gathered retrospectively after the individuals from whom the images were taken have been diagnosed with breast cancer. In some embodiments, the second AI model is a model that has been trained to classify images as associated with a likely current diagnosis of breast cancer or not associated with a likely current diagnosis of breast cancer.

In some embodiments, the current mammograms are images from one or more first users who received positive cancer diagnoses (e.g., from screenings, medical imaging, or other test results which indicate that they have cancer) within a first time period from the current mammograms being taken. As an example, the current mammograms may be medical images taken from one or more first users who were diagnosed with breast cancer after receiving a positive health screening and biopsy confirming, or providing, a cancer diagnosis within a 12 month time period after the mammogram was taken. Only the images from a breast (e.g., left breast or right breast) which is diagnosed with having cancer are included in the current mammograms set of images. The second AI model may also be trained using images which have been labeled as indicating a negative diagnosis (e.g., no breast cancer). The negative diagnosis images may be gathered from patients for whom the current screening exam (medical images and other testing) is negative (e.g., negative for cancer or benign) and follow-up screening exams (medical images and/or other testing) for a 24-48 month period are negative.

In some embodiments, the prior mammograms are a set of images obtained for training the first AI model to classify images as indicating a likelihood of the user to develop breast cancer in the future (positive) or not indicating a likelihood of the user to develop breast cancer in the future (negative). The images in the prior mammograms set of images may be images from one or more second users who received negative screenings (e.g., indicating that the users do not have breast cancer) for at least second time period following the images from the prior mammograms being taken and later receive a positive diagnosis (e.g., indicating that the users do have the breast cancer).

As an example, the prior mammograms may be medical images taken from one or more second users who were determined to not have breast cancer (e.g., either based on the medical images and/or other testing) for at least a 24-48 month time period after the time that the medical images in the set of prior mammograms were taken, and after that time period received a positive diagnosis (e.g., indicating that the users do have breast cancer, either by medical imaging, other diagnostic testing, or both).

In some embodiments, the one or more second users from whom the images in the prior mammograms set of images is obtained may partially, or completely, overlap with the one or more first users from whom the images in the current mammograms set of images is obtained. For example, user A may have 10 yearly health screenings during which mammograms are obtained. If in year 10, user A is diagnosed with breast cancer, the year 10 medical image may be included among the images of set of images from current mammograms. The year 1 through year 7 medical images may be included among the images of the set of images from the prior mammograms. In some embodiments, the first AI model may also be trained using images which have been labeled as not indicating a likelihood of the user to develop a breast cancer (negative). The negative labeled images may be gathered from users who it was determined do not have breast cancer (e.g., by the medical images and/or other testing) for a time period greater than 48 months.

In some embodiments, the AI system may receive a classification output, where the classification output provides a classification by the first AI model, the second AI model, or both models. In some embodiments, the classification output may be an output of the AI system from the first AI model which provides information indicating a likelihood of the user to develop breast cancer in the future. In some embodiments, the classification output may be an output from the second AI model which indicates a likely current breast cancer diagnosis.

For example, the classification output may be a numerical value which indicates that the image is classified as: indicating a likelihood of the user to develop breast cancer in the future, indicating a likely current breast cancer diagnosis, or indicating both a likelihood of the user to develop breast cancer in the future and indicating a likely current breast cancer diagnosis. For example, a medical image from a user may be provided to the AI system. The mammogram may show a tumor and an abnormality, which may develop into a tumor. The AI system may provide an output classifying the mammogram as indicating a likelihood of the user to develop breast cancer in the future based on the first AI model classifying the abnormality on the breast as likely to develop into tumors in the future. The AI system may provide an output classifying the mammogram as indicating a likely current breast cancer diagnosis based on the second AI model classifying the tumors as indicative of a breast cancer diagnosis.

In some embodiments, an AI system may receive training images. In some embodiments, each of the training images may be linked in a group, and the group may include training images of one training user. For example, the training images from a first training user may be linked in a group, and the training images may include prior mammograms (described below) and/or current mammograms (described below) from the first training user. The prior mammograms and/or the current mammograms may include any number of current or prior mammograms, different mammograms which include images of the breast from different angles, and incomplete sets of mammograms.

For example, the first training user may have four current mammograms that were images taken from different angles and which were taken 10 months prior to the first training user receiving a breast cancer diagnosis. The first training user may have 11 prior mammograms, where four of the prior mammograms where taken 58 months before the first training user received the breast cancer diagnosis; another four images were taken 70 months before the first training user received the breast cancer diagnosis; and the remaining three images were taken 82 months before the first training user received the breast cancer diagnosis. The four prior mammograms taken 58 months before the first training user received the breast cancer diagnosis and the four prior mammograms taken 70 months before the first training user received the breast cancer diagnosis may include images taken from four different angles. The three prior mammograms taken 82 months before the first training user received the breast cancer diagnosis may include images taken from only three of the four different angles that the other mammograms taken in different years included. The training image from the first training user are linked in a group so that the AI system can classify training images as showing a likelihood of future breast cancer development or a likelihood of current cancer.

In some embodiments, an AI system may register the grouped training images. Registering the training images may involve mathematical processing of data obtained from the images so that if more than one of the grouped training images (e.g., a first training image and a second training image) include an image of a certain region of the body, those group training images (e.g., the first training image and a second training image) are identified. In some embodiments, the first training image may be aligned with the second training image. Aligning the two images involves identifying that a first portion of the first training image corresponds with a second portion of the second training image. In some embodiments, the training images received by the AI system may also be preprocessed to control the quality of the data provided to the AI models. The preprocessing may involve various techniques, including but not limited to: cleaning, instance selection, normalization, transformation, etc. of the data.

In some embodiments, an AI system may obtain a first set of feature vectors from a first AI model trained to classify images as indicate a likelihood of the user to develop breast cancer in the future using training images from the set of prior mammograms. In some embodiments, the AI system may obtain a second set of feature vectors from a second AI model trained to indicate a likely current diagnosis of breast cancer using training images from the set of current mammograms.

In some embodiments, the prior mammograms and current mammograms images are digital mammograms. In some embodiments, the first set of feature vectors and the second set of feature vectors may include numeric features, where the features are measurable characteristics of the training images used to train the first AI model and second AI model, respectively. In some embodiments, the first AI model is a CNN.

In some embodiments, the first set of feature vectors are n-dimensional vectors of numerical features that represent characteristics of the prior mammogram set of training images which indicate a likelihood of the user to develop breast cancer in the future (e.g., an abnormality such as a lesion). In some embodiments, the second AI model is a CNN. In some embodiments, the second set of feature vectors are n-dimensional vectors of numerical features that represent characteristics of the current mammogram set of training images which indicate a likely current diagnosis of breast cancer (e.g., a tumor).

In some embodiments, an AI system may apply a feature selection algorithm to the first set of feature vectors and the second set of feature vectors. In some embodiments, the feature selection algorithm identifies which features from the first set of feature vectors and the second set of feature vectors should be used to create a predictive model predicting a likelihood of the user to develop breast cancer in the future or a likely current diagnosis of breast cancer. In some embodiments, the feature selection algorithm may be a form of machine learning. Feature selection algorithms can be used to identify and remove unneeded, irrelevant, and/or redundant attributes from data that do not contribute to the accuracy of the predictive model or may decrease the accuracy of the model.

In some embodiments, the feature selection algorithm may include filter methods of feature selection (e.g., application of statistical measures to assign a scoring to each feature and then ranking the features by their score). The feature selection algorithm may include wrapper methods (e.g., recursive feature elimination algorithms, etc.) of feature selection. For example, the wrapper methods may consider the selection of a set of features as a search problem, where different combinations are prepared, evaluated and compared to other combinations.

In some embodiments, a predictive model may be used to evaluate a combination of features and assign a score based on model accuracy. As an example, the search process may be methodical (such as a best-first search), stochastic (such as a random hill-climbing algorithm), or use heuristics (such as forward and backward passes to add and remove features). In some embodiments, the feature selection algorithm may include embedded methods of feature selection (e.g., regularization or penalization methods such as LASSO, Elastic Net and Ridge Regression, etc.).

It is noted that embedded methods learn which features best contribute to the accuracy of the model while the model is being created. For example, the first set of features vectors and the second set of feature vectors may be input into the feature selection algorithm and a set of features (e.g., a subset of the second set of feature vectors combined with the first set of feature vectors) more relevant to the accuracy of predicting a likelihood of the user to develop breast cancer in the future or a likely current diagnosis of breast cancer may be output.

In some embodiments, an AI system may input feature vectors selected using the feature selection algorithm into a classification AI model. In some embodiments, the classification AI model may provide a first prediction score output indicating likelihood of future breast cancer development and a second classification score indicating likelihood of current cancer. In some embodiments, the classification AI model may be any deep learning model used for image classification, including CNNs and recurrent neural networks ("RNN") which may detect the set of features (e.g., the features output from the feature selection algorithm) in images. After the AI system is trained and medical images from a patient are input into the AI system, the AI system has the benefit of informing a healthcare professional about whether the patient is likely to currently have cancer or about whether the patient is likely to develop cancer in the future from the same inputs.

In some embodiments, the classification AI model is a Long Short Term Memory ("LSTM") model of deep learning using RNN architecture. A LSTM model may be advantageous because LSTM models allow the grouped training images to include a varying number of medical images. For example, one group of training images from a one training user may have 10 medical images and another group of training images from another training user may have 31 medical images. The variable number of medical images may result from training users having different numbers of periodic screening exams over different lengths of time. The variable number of medical images may also result from some medical images being lost over time. Allowing variable numbers of training images per group of training images allows a greater amount of data to be used to train the deep learning model. Additionally, after the deep learning model is trained, it may be used by different users where different users input different numbers of medical images into the deep learning model to determine whether the medical images indicate that a user is likely to have a medical condition or likely to develop a medical condition in the future.

In some embodiments, the current mammograms are a set of images obtained for training the second AI model which have been gathered retrospectively after the individuals from whom the images were taken have been diagnosed with breast cancer. In some embodiments, the second AI model is a model that has been trained to classify images as associated with a diagnosis of breast cancer or not corresponding to diagnosis of breast cancer.

In some embodiments, the current mammograms are images from one or more users who received positive cancer diagnoses (e.g., from screenings, medical imaging, or other test results which indicate that they have cancer) within a first time period from the current mammograms being taken. As an example, the current health screenings may be mammograms taken from users who were diagnosed with breast cancer after receiving a positive health screening and biopsy providing, or confirming, the cancer diagnosis within a 12 month time period after the mammogram (e.g., the current health screening) was taken. In some embodiments, only the images from the breast which is diagnosed with having cancer is included in the current mammograms set of images. The second AI model may also be trained using images which have been labeled as negative diagnosis, or not having cancer. The negative diagnosis images may be gathered from patients for whom the current screening exam (medical images and other testing) is negative (e.g., negative for cancer or benign) and follow-up screening exams (medical images and other testing) for 24-48 months are negative.

In some embodiments, the prior mammograms are a set of images obtained for training the first AI model to classify images as indicating a likelihood of the user to develop breast cancer in the future (positive) or not indicating a likelihood of the user to develop breast cancer in the future (negative). In some embodiments, the prior mammograms are a set of images obtained for training the first AI model to classify images as indicating a likelihood of the user to develop breast cancer in the future (positive) or not indicating a likelihood of the user to develop breast cancer in the future (negative). The images in the prior mammograms set of images may be images from one or more second users who received negative screenings (e.g., indicating that the users do not have breast cancer) for at least second time period following the images from the prior mammograms being taken and later receive a positive diagnosis (e.g., indicating that the users do have the breast cancer).

As an example, the prior mammograms may be medical images taken from one or more second users who were determined to not have breast cancer (e.g., either based on the medical images and/or other testing) for at least a 24-48 month time period after the time that the medical images in the set of prior mammograms were taken, and after that time period received a positive diagnosis (e.g., indicating that the users do have breast cancer, either by medical imaging, other diagnostic testing, or both).

The one or more second users from whom the images in the prior mammograms set of images is obtained may partially, or completely, overlap with the one or more first users from whom the images in the current mammograms set of images is obtained. For example, user A may have 10 yearly health screenings during which mammograms are obtained. If in year 10, user A is diagnosed with breast cancer, the year 10 medical image may be included among the images of set of images from current mammograms. The year 1 through year 7 medical images may be included among the images of the set of images from the prior mammograms. In some embodiments, the first AI model may also be trained using images which have been labeled as not indicating a likelihood of the user to develop a breast cancer (negative). The negative labeled images may be gathered from users who it was determined do not have breast cancer (e.g., by the medical images and/or other testing) for a time period greater than 48 months.

In some embodiments, the second AI model is trained by, after the first AI model is trained to classify images, using transfer learning to apply the weights from the first AI model to initialize the second AI model. In other words, the second AI model is loaded using the pretrained weights from the first AI model.

Referring now to FIG. 1, a block diagram of a system 100 to improve health screenings using AI is illustrated. System 100 includes a user device 102 and a network 104 which are configured to be in communication with each other. In some embodiments, first device 102 may be any device that contains a processor configured to perform one or more of the functions or steps described herein this disclosure.

Network 104 includes an AI system 106 which includes first AI model 108, second AI model 110, and classification AI model 112.

In some embodiments, AI system 106 has been trained to improve health screenings. In some embodiments, the first AI model 108 has been trained using labeled training images from prior health screenings to classify images. In some embodiments, the second AI model 110 has been trained using labeled training images from current health screenings to classify images. In some embodiments, the classification AI model 112 has been trained to classify images as having features selected, using a feature selection algorithm, from a first set of feature vectors obtained from the first AI model 108 and a second set of feature vectors obtained from a second AI model 110. In some embodiments, each of the first AI model 108, second AI model 110, and classification AI model 112 are trained and/or perform the functions which were previously discussed above and discussed throughout this disclosure.

In some embodiments, a user inputs a user image into the user device 102 which is in communication with the AI system 106. In some embodiments, the AI system 106 receives the user image and subsequently receives a classification output from the classification AI model 112, the first AI mode 108, or the second AI model 110 which the AI system 106 then communicates (e.g., pushes, forwards, etc.) to the user device 102. In some embodiments, the classification output indicates a likely current (e.g., breast cancer) diagnosis or a likelihood of the user to develop breast cancer in the future.

Figure 2A:
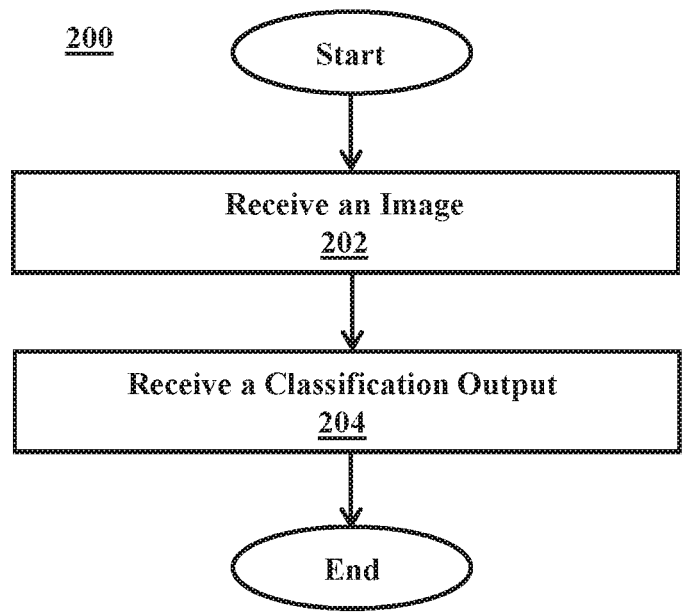
FIG. 2A is a flowchart of an exemplary method for improved health screening using artificial intelligence, in accordance with aspects of the present disclosure.

Referring now to FIG. 2A, illustrated is a flowchart of an exemplary method 200 for improving health screening using artificial intelligence, in accordance with embodiments of the present disclosure. In some embodiments, a processor of a system (e.g., an AI system) may perform the operations of the method 200. In some embodiments, method 200 begins at operation 202. At operation 202, the AI system receives an image. In some embodiments, the AI system includes a first AI model 108 trained using labeled training images from prior health screenings to classify images and a second AI model 110 trained using labeled training images from current health screenings to classify images. In some embodiments, method 200 proceeds to operation 204, where the AI system receives a classification output.

Figure 2B:
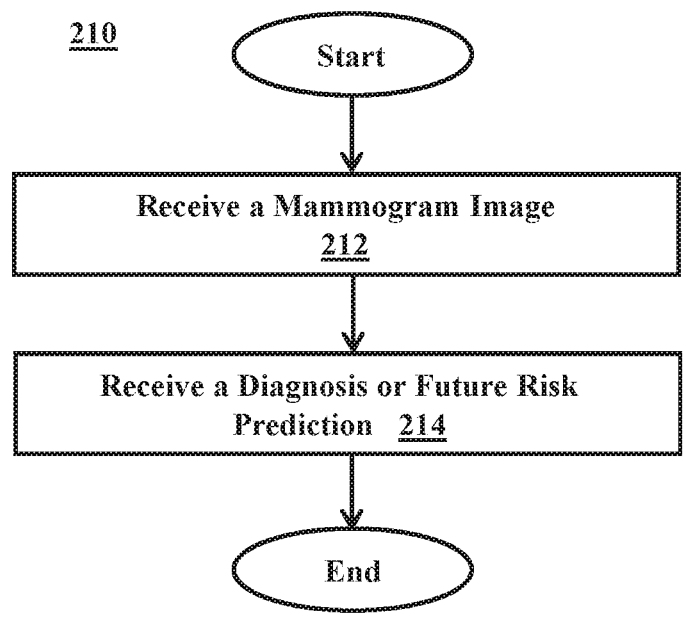
FIG. 2B is a flowchart of an exemplary method for improved breast cancer screening using artificial intelligence, in accordance with aspects of the present disclosure.

Referring now to FIG. 2B, illustrated is a flowchart of an exemplary method 210 for improving breast cancer screenings using artificial intelligence, in accordance with embodiments of the present disclosure. In some embodiments, a processor of a system (e.g., an AI system) may perform the operations of the method 210. In some embodiments, method 210 begins at operation 212. At operation 212, the AI system receives a user image, as depicted the user image is a mammogram image. In some embodiments, the AI system includes a first AI model 108 trained using labeled training images including images from prior mammograms to classify mammogram images and a second AI model 110 trained using labeled training images including images from current mammograms to classify mammogram images. In some embodiments, the second AI model 110 is initialized using the weights of the first AI model 108 using transfer learning. In some embodiments, method 210 proceeds to operation 214, where the AI system receives a classification output indicating a likely current breast cancer diagnosis or a (predicted) likelihood of the user to develop breast cancer in the future.

Figure 2C:
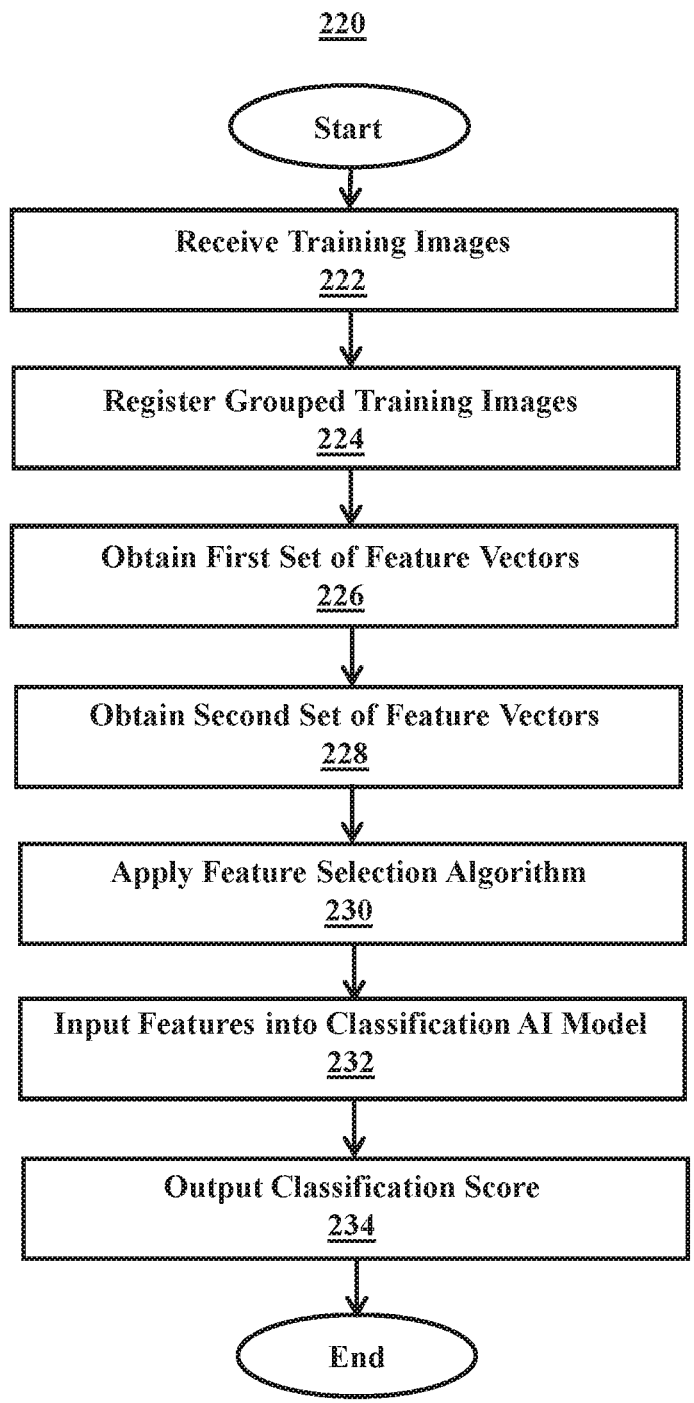
FIG. 2C is a flowchart of an exemplary method for training an artificial intelligence for improved health screening, in accordance with aspects of the present disclosure.

Referring now to FIG. 2C, illustrated is a flowchart of an exemplary method 220 for training an artificial intelligence system for improved health screening, in accordance with embodiments of the present disclosure. In some embodiments, a processor of a system (e.g., an AI system) may perform the operations of the method 220. In some embodiments, method 220 begins at operation 222. At operation 222, the AI system receives training images. In some embodiments, each of the training images is linked in a group, where the group includes training images of one training user. In some embodiments, method 220 proceeds to operation 224, where the AI system registers the grouped training images. In some embodiments, a first training image in the group is aligned so that the same region of space in the first training image can be compared to the same region of space in a second training image in the group. In some embodiments, method 220 proceeds to operation 226 where the AI system obtains a first set of feature vectors from a first AI model trained to classify images using training images from prior mammograms. In some embodiments, method 220 proceeds to operation 228 where the AI system obtains a second set of feature vectors from a second AI model trained to classify images using training images from current mammograms.

In some embodiments, method 220 proceeds to operation 230 where the AI system applies a feature selection algorithm to the first set of feature vectors and the second set of feature vectors. In some embodiments, method 220 proceeds to operation 232 where the AI system inputs feature vectors selected using the feature selection algorithm into a classification AI model. In some embodiments, method 220 proceeds to operation 234 where the AI system outputs a first prediction score indicating a likelihood of future breast cancer development and a second classification score indicating likelihood of current cancer.

As discussed in more detail herein, it is contemplated that some or all of the operations of the methods 200, 210, and 220 may be performed in alternative orders or may not be performed at all; furthermore, multiple operations may occur at the same time or as an internal part of a larger process.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of portion independence in that the consumer generally has no control or knowledge over the exact portion of the provided resources but may be able to specify portion at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 3A:
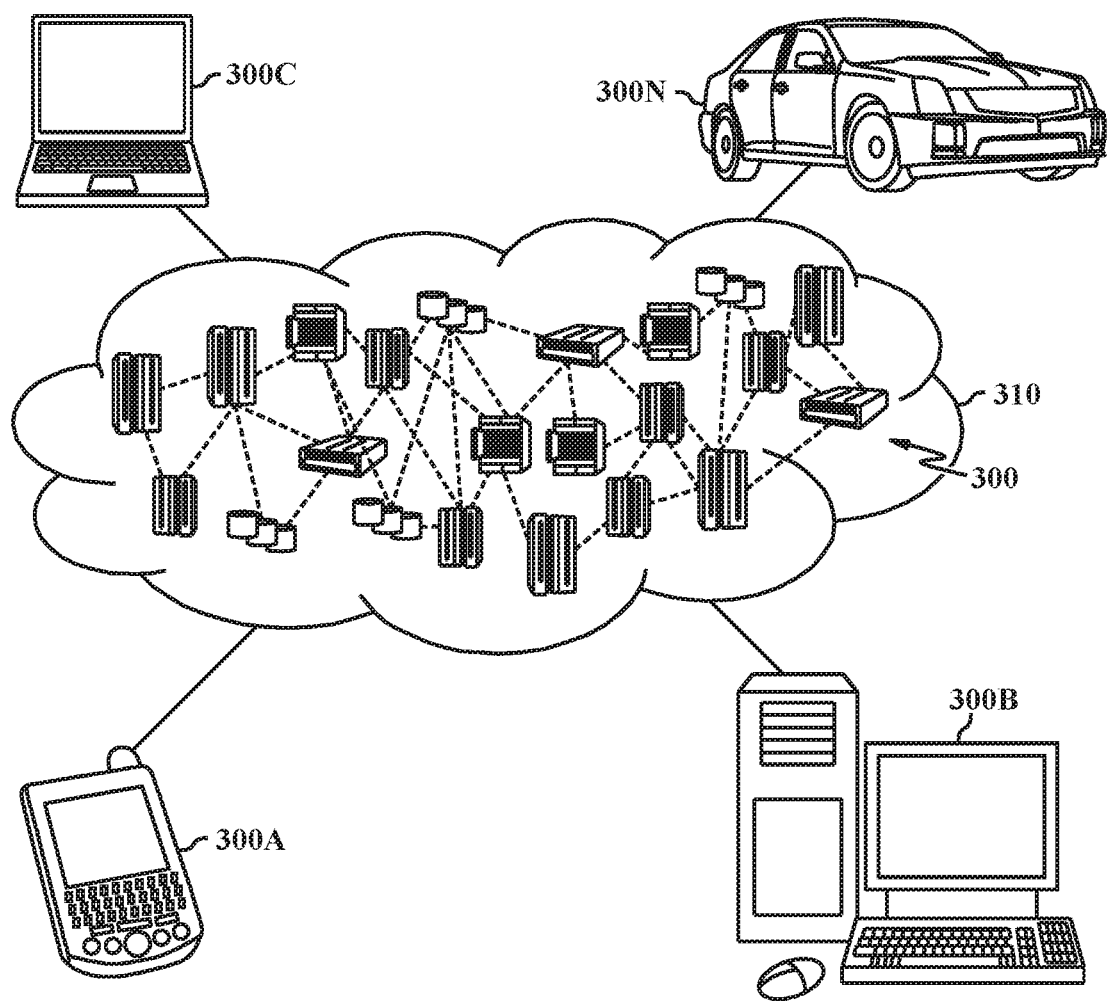
FIG. 3A illustrates a cloud computing environment, in accordance with aspects of the present disclosure.

FIG. 3A, illustrated is a cloud computing environment 310 is depicted. As shown, cloud computing environment 310 includes one or more cloud computing nodes 300 with which local computing devices used by cloud consumers, such as, for example, personal digital assistant (PDA) or cellular telephone 300A, desktop computer 300B, laptop computer 300C, and/or automobile computer system 300N may communicate. Nodes 300 may communicate with one another. They may be grouped (not shown) physically or virtually, in one or more networks, such as Private, Community, Public, or Hybrid clouds as described hereinabove, or a combination thereof.

This allows cloud computing environment 310 to offer infrastructure, platforms and/or software as services for which a cloud consumer does not need to maintain resources on a local computing device. It is understood that the types of computing devices 300A-N shown in FIG. 3A are intended to be illustrative only and that computing nodes 300 and cloud computing environment 310 can communicate with any type of computerized device over any type of network and/or network addressable connection (e.g., using a web browser).

Figure 3B:
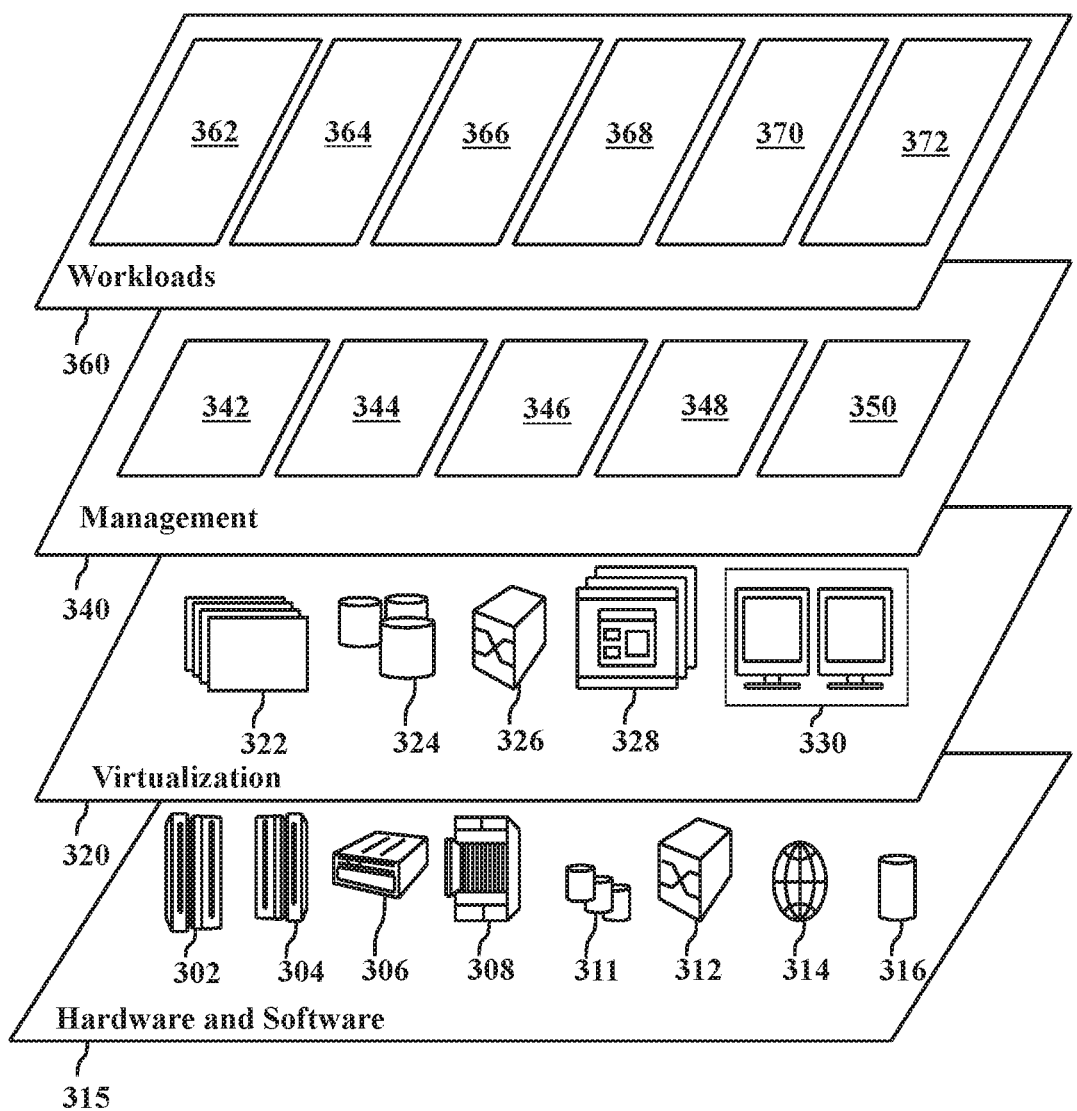
FIG. 3B illustrates abstraction model layers, in accordance with aspects of the present disclosure.

FIG. 3B, illustrated is a set of functional abstraction layers provided by cloud computing environment 310 (FIG. 3A) is shown. It should be understood in advance that the components, layers, and functions shown in FIG. 3B are intended to be illustrative only and embodiments of the disclosure are not limited thereto. As depicted below, the following layers and corresponding functions are provided.

Hardware and software layer 315 includes hardware and software components. Examples of hardware components include: mainframes 302; RISC (Reduced Instruction Set Computer) architecture based servers 304; servers 306; blade servers 308; storage devices 311; and networks and networking components 312. In some embodiments, software components include network application server software 314 and database software 316.

Virtualization layer 320 provides an abstraction layer from which the following examples of virtual entities may be provided: virtual servers 322; virtual storage 324; virtual networks 326, including virtual private networks; virtual applications and operating systems 328; and virtual clients 330.

In one example, management layer 340 may provide the functions described below. Resource provisioning 342 provides dynamic procurement of computing resources and other resources that are utilized to perform tasks within the cloud computing environment. Metering and Pricing 344 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 346 provides access to the cloud computing environment for consumers and system administrators. Service level management 348 provides cloud computing resource allocation and management such that required service levels are met. Service Level Agreement (SLA) planning and fulfillment 350 provide pre-arrangement for, and procurement of, cloud computing resources for which a future requirement is anticipated in accordance with an SLA.

Workloads layer 360 provides examples of functionality for which the cloud computing environment may be utilized. Examples of workloads and functions which may be provided from this layer include: mapping and navigation 362; software development and lifecycle management 364; virtual classroom education delivery 366; data analytics processing 368; transaction processing 370; and improved health screening using AI 372.

Figure 4:
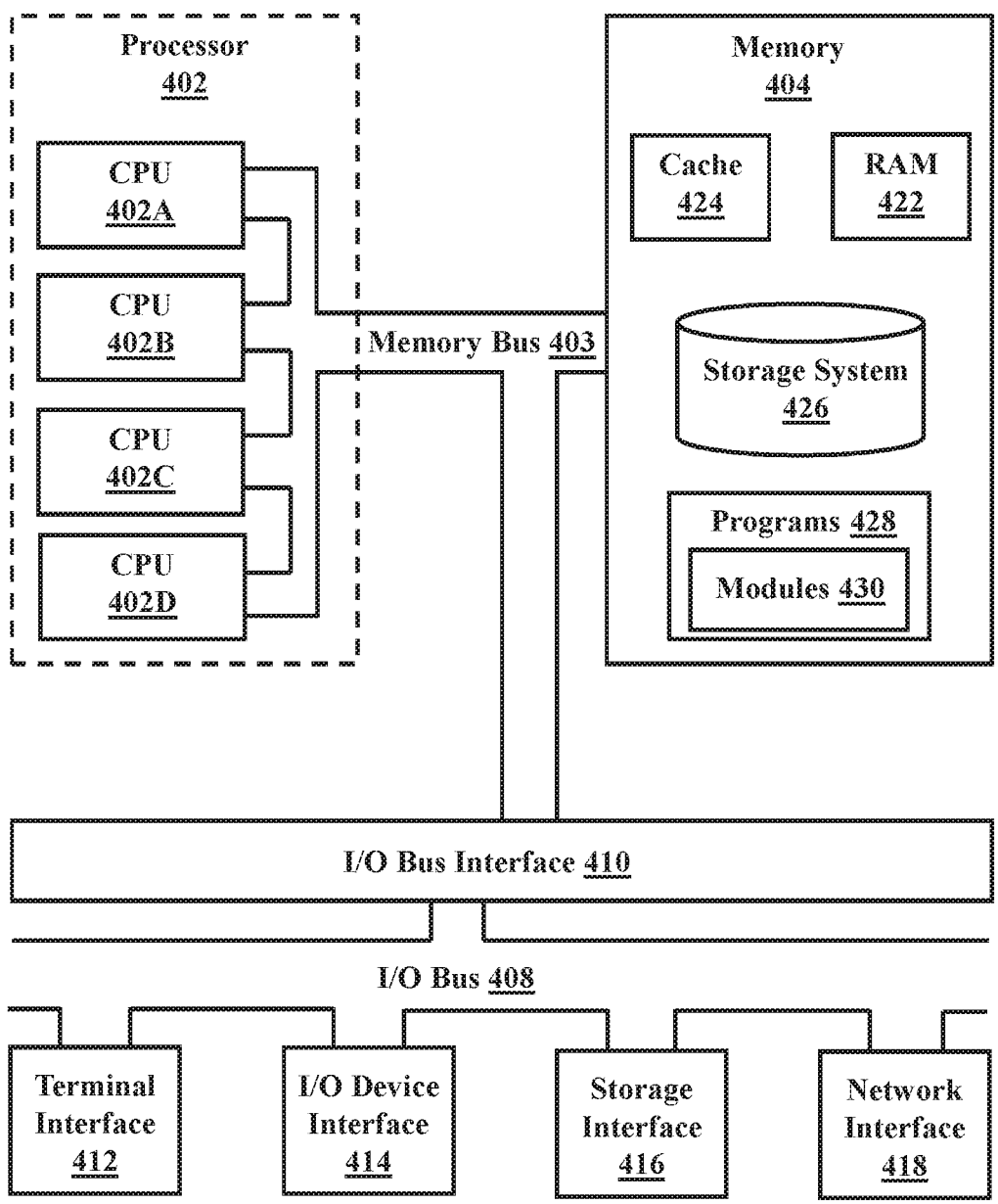
FIG. 4 illustrates a high-level block diagram of an example computer system that may be used in implementing one or more of the methods, tools, and modules, and any related functions, described herein, in accordance with aspects of the present disclosure.

FIG. 4, illustrated is a high-level block diagram of an example computer system 401 that may be used in implementing one or more of the methods, tools, and modules, and any related functions, described herein (e.g., using one or more processor circuits or computer processors of the computer), in accordance with embodiments of the present disclosure. In some embodiments, the major components of the computer system 401 may comprise one or more CPUs 402, a memory subsystem 404, a terminal interface 412, a storage interface 416, an I/O (Input/Output) device interface 414, and a network interface 418, all of which may be communicatively coupled, directly or indirectly, for inter-component communication via a memory bus 403, an I/O bus 408, and an I/O bus interface unit 410.

The computer system 401 may contain one or more general-purpose programmable central processing units (CPUs) 402A, 402B, 402C, and 402D, herein generically referred to as the CPU 402. In some embodiments, the computer system 401 may contain multiple processors typical of a relatively large system; however, in other embodiments the computer system 401 may alternatively be a single CPU system. Each CPU 402 may execute instructions stored in the memory subsystem 404 and may include one or more levels of on-board cache.

System memory 404 may include computer system readable media in the form of volatile memory, such as random access memory (RAM) 422 or cache memory 424. Computer system 401 may further include other removable/non-removable, volatile/non-volatile computer system storage media. By way of example only, storage system 426 can be provided for reading from and writing to a non-removable, non-volatile magnetic media, such as a "hard drive." Although not shown, a magnetic disk drive for reading from and writing to a removable, non-volatile magnetic disk (e.g., a "floppy disk"), or an optical disk drive for reading from or writing to a removable, non-volatile optical disc such as a CD-ROM, DVD-ROM or other optical media can be provided. In addition, memory 404 can include flash memory, e.g., a flash memory stick drive or a flash drive. Memory devices can be connected to memory bus 403 by one or more data media interfaces. The memory 404 may include at least one program product having a set (e.g., at least one) of program modules that are configured to carry out the functions of various embodiments.

One or more programs/utilities 428, each having at least one set of program modules 430 may be stored in memory 404. The programs/utilities 428 may include a hypervisor (also referred to as a virtual machine monitor), one or more operating systems, one or more application programs, other program modules, and program data. Each of the operating systems, one or more application programs, other program modules, and program data or some combination thereof, may include an implementation of a networking environment. Programs 428 and/or program modules 430 generally perform the functions or methodologies of various embodiments.

Although the memory bus 403 is shown in FIG. 4 as a single bus structure providing a direct communication path among the CPUs 402, the memory subsystem 404, and the I/O bus interface 410, the memory bus 403 may, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 410 and the I/O bus 408 are shown as single respective units, the computer system 401 may, in some embodiments, contain multiple I/O bus interface units 410, multiple I/O buses 408, or both. Further, while multiple I/O interface units are shown, which separate the I/O bus 408 from various communications paths running to the various I/O devices, in other embodiments some or all of the I/O devices may be connected directly to one or more system I/O buses.

In some embodiments, the computer system 401 may be a multi-user mainframe computer system, a single-user system, or a server computer or similar device that has little or no direct user interface, but receives requests from other computer systems (clients). Further, in some embodiments, the computer system 401 may be implemented as a desktop computer, portable computer, laptop or notebook computer, tablet computer, pocket computer, telephone, smartphone, network switches or routers, or any other appropriate type of electronic device.

It is noted that FIG. 4 is intended to depict the representative major components of an exemplary computer system 401. In some embodiments, however, individual components may have greater or lesser complexity than as represented in FIG. 4, components other than or in addition to those shown in FIG. 4 may be present, and the number, type, and configuration of such components may vary.

As discussed in more detail herein, it is contemplated that some or all of the operations of some of the embodiments of methods described herein may be performed in alternative orders or may not be performed at all; furthermore, multiple operations may occur at the same time or as an internal part of a larger process.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present disclosure has been described in terms of specific embodiments, it is anticipated that alterations and modification thereof will become apparent to the skilled in the art. Therefore, it is intended that the following claims be interpreted as covering all such alterations and modifications as fall within the true spirit and scope of the disclosure.

What is claimed is:

1. A method for improving health screening using artificial intelligence (AI), comprising:
  receiving a user image by an AI system, wherein the AI system includes:
    a first AI model trained using labeled training images from prior health screenings to predict a medical condition, wherein the first AI model generates a first set of feature vectors based on the user image;
    a second AI model trained using labeled training images from current health screenings to classify images, wherein the second AI model generates a second set of feature vectors based on the user image;

a feature selection algorithm that selects feature vectors from at least one of the first set of feature vectors or the second set of feature vectors to generate selected feature vectors; and a classification AI model that processes the selected feature vectors to generate a classification output that comprises a prediction score indicative of a likelihood of the medical condition; and receiving the classification output from the AI system.

2. The method of claim 1, wherein the second AI model is trained by, after the first AI model is trained to predict the medical condition, using transfer learning to apply the weights from the first AI model to initialize the second AI model.

3. The method of claim 1, wherein the images from the current health screenings are images from one or more first users who received positive diagnoses within a first time period from the current health screenings being taken.

4. The method of claim 1, wherein the images from the prior health screenings are images from one or more second users who received negative screenings for at least a second time period following the prior health screenings being taken and later received positive diagnoses.

5. The method of claim 1, wherein the user image is a digital x-ray.

6. The method of claim 1, wherein the first AI model is a convolutional neural network.

7. The method of claim 1, wherein the second AI model is a convolutional neural network.

8. A method for improving breast cancer screening using artificial intelligence (AI), comprising:
receiving a user image by an AI system, the AI system including:
a first AI model trained using labeled training images including images from prior mammograms to predict cancer, wherein the first AI model generates a first set of feature vectors based on the user image;
a second AI model trained using labeled training images including images from current mammograms to classify mammogram images, wherein the second AI model generates a second set of feature vectors based on the user image, and wherein the second AI model is initialized using the weights of the first AI model using transfer learning;
a feature selection algorithm that selects feature vectors from at least one of the first set of feature vectors or the second set of feature vectors to generate selected feature vectors; and
a classification AI model that processes the selected feature vectors to generate a classification output that comprises a prediction score indicative of a current breast cancer diagnosis or a likelihood of the user to develop breast cancer in the future; and
receiving the classification output.

9. The method of claim 8, wherein the user image is a digital mammogram.

10. The method of claim 9, wherein the current mammograms are one or more medical images from one or more first users who received positive cancer diagnoses within a first time period from the medical images being taken.

11. The method of claim 10, wherein the prior mammograms are one or more further medical images from one or more second users who received negative cancer screenings for at least a second time period following the medical image being taken and later received positive diagnoses.

12. The method of claim 8, wherein the first AI model and the second AI model are convolutional neural networks.

13. A method for training an artificial intelligence (AI) system for improved health screening, the method comprising:
receiving training images, wherein each of the training images is linked in a group, and wherein the group includes training images of one training user;
registering grouped training images, wherein registering grouped training images involves aligning a first training image so that the same region of 2D space in the first training image in the group can be compared to a same region of 2D space in a second training image in the group;
obtaining a first set of feature vectors from a first AI model trained to predict cancer using training images from prior mammograms;
obtaining a second set of feature vectors from a second AI model trained to classify images using training images from current mammograms;
applying a feature selection algorithm to the first set of feature vectors and the second set of feature vectors;
inputting feature vectors selected using the feature selection algorithm into a classification AI model; and
providing an output, wherein the output includes a first prediction score indicating a likelihood of future breast cancer development and a second classification score indicating likelihood of current cancer.

14. The method of claim 13, wherein the current mammograms are one or more medical images from one or more first users who received positive diagnoses within a first time period from the medical images being taken.

15. The method of claim 14, wherein the prior mammograms are one or more further medical images from one or more second users who received negative screenings for a second time period following the medical images being taken and later received positive diagnoses.

16. The method of claim 13, wherein the second AI model is trained by, after the first AI model is trained to predict cancer, using transfer learning to apply the weights from the first AI model to initialize the second AI model.

17. The method of claim 13, wherein the first AI model and the second AI model are convolutional neural networks.

18. The method of claim 13, wherein the classification AI model is a Long Short-Term Memory.

19. A system comprising:
a memory; and
a processor in communication with the memory, the processor being configured to perform operations comprising:
receiving training images, wherein each of the training images is linked in a group, and wherein the group includes training images of one training user;
obtaining a first set of feature vectors from a first AI model trained to predict cancer using training images from prior mammograms;
obtaining a second set of feature vectors from a second AI model trained to classify images using training images from current mammograms;
applying a feature selection algorithm to the first set of feature vectors and the second set of feature vectors;
inputting feature vectors selected using the feature selection algorithm into a classification AI model; and
providing an output, wherein the output includes a first prediction score indicating a likelihood of future breast cancer development and a second classification score indicating likelihood of current cancer.

20. The system of claim 19, wherein the second AI model is trained by, after the first AI model is trained to classify images, using transfer learning to apply the weights from the first AI model to initialize the second AI model.

21. The system of claim 19, wherein the current mammograms are one or more medical images from one or more first users who received positive cancer diagnoses within a first time period from the medical images being taken.

22. The system of claim 19, wherein the prior mammograms are one or more further medical images from one or more second users who received negative cancer screenings for at least a second time period following the medical image being taken and later received positive diagnoses.

23. A computer program product comprising a computer readable storage medium having program instructions embodied therewith, the program instructions executable by a processor to cause the processor to perform operations, the operations comprising:
  receiving training images, wherein each of the training images is linked in a group, and wherein the group includes training images of one training user;
  obtaining a first set of feature vectors from a first AI model trained to predict cancer using training images from prior mammograms;
  obtaining a second set of feature vectors from a second AI model trained to classify images using training images from current mammograms;
  applying a feature selection algorithm to the first set of feature vectors and the second set of feature vectors;
  inputting feature vectors selected using the feature selection algorithm into a classification AI model; and
  providing an output, wherein the output includes a first prediction score indicating a likelihood of future breast cancer development and a second classification score indicating likelihood of current cancer.

24. The computer program product of claim 23, wherein the current mammograms are one or more medical images from one or more first users who received positive cancer diagnoses within a first time period from the medical images being taken.

25. The computer program product of claim 23, wherein the prior mammograms are one or more further medical images from one or more second users who received negative cancer screenings for at least a second time period following the medical image being taken and later received positive diagnoses.

* * * * *